(12) United States Patent
Cao et al.

(10) Patent No.: US 6,967,078 B1
(45) Date of Patent: Nov. 22, 2005

(54) INTERACTION OF SMAD6 WITH HOX PROTEINS AND USES THEREOF

(76) Inventors: Xu Cao, 3508 Oakdale Dr., Birmingham, AL (US) 35223; Xingming Shi, 1032-C 14th St. South, Birmingham, AL (US) 35205; Shuting Bai, 665 Idlewild Cir., Birmingham, AL (US) 35205

( * ) Notice: Subject to any disclaimer, the term of this patent is extended or adjusted under 35 U.S.C. 154(b) by 788 days.

(21) Appl. No.: 09/631,411

(22) Filed: Aug. 3, 2000

Related U.S. Application Data

(60) Provisional application No. 60/147,161, filed on Aug. 4, 1999.

(51) Int. Cl.[7] .......................... C12Q 1/68; C07H 21/04; C12N 15/00
(52) U.S. Cl. ......................... 435/6; 435/69.1; 435/91.1; 536/23.1; 536/23.5
(58) Field of Search .......................... 435/6, 69.1, 91.1, 435/455; 536/23.1, 23.5, 24.1, 24.5

(56) References Cited

OTHER PUBLICATIONS

Hata, A., et al., *Smad6 Inhibits BMP/Smad1 Signaling by Specifically Competing With the Smad4 Tumor Supressor.* Genes & Development vol. 12, 1998, pp. 186-197.

Ishisaki, A., et al. *Differential Inhibition of Smad6 and Smad7 on Bone Morphogenetic Protein and Activin-Mediated Growth Arrest and Apoptosis in B Cells.* The Journal of Biological Chemistry vol. 274, 1999, pp. 13637-13642.

*Primary Examiner*—Sean McGarry
(74) *Attorney, Agent, or Firm*—Benjamin Aaron Adler

(57) ABSTRACT

The present invention describes a novel interaction between Smad6 and the Hox genes in nuclear transcriptional regulation following BMP signal transduction. The present invention further provides methods of using this novel Smad6/Hox protein interaction to regulate gene expression, regulate bone formation and control osteoporosis. Further provided are methods of screening for compounds that interfere with the novel Smad6/Hox protein interaction, thereby resulting in expression of a Hox protein-repressed gene and/or stimulating bone formation.

4 Claims, 4 Drawing Sheets

| | 1 | 2 | 3 | 4 | 5 | 6 | 7 | 8 |
|---|---|---|---|---|---|---|---|---|
| ALK3 | − | − | − | − | + | − | − | + |
| HA-Hoxc-8 | − | − | + | + | + | + | + | + |
| Flag-Smad6c | − | + | − | + | + | − | − | − |
| Flag-Smad6(N+L) | − | − | − | − | − | + | − | − |
| Flag-Smad6 | − | − | − | − | − | − | + | + |

IP: Anti-Flag
IB: Anti-HA

IB: Anti-Flag

IB: Anti-HA

A

B

INTERACTION OF SMAD6 WITH HOX PROTEINS AND USES THEREOF

CROSS-REFERENCE TO RELATED APPLICATION

This non-provisional patent application claims benefit of provisional patent application U.S. Ser. No. 60/147,161, filed Aug. 4, 1999, now abandoned.

BACKGROUND OF THE INVENTION

1. Field of the Invention

The present invention relates generally to the field of signal transduction, transcriptional regulation and bone physiology. More specifically, the present invention relates to the role by which Smad6 interacts with nuclear Hox proteins during bone morphogenetic protein (BMP) signal transduction.

2. Description of the Related Art

Members of TGF-β superfamily transduce their signals into the cell through a family of mediator proteins called Smads. Receptor-regulated Smad1, Smad5 and Smad8 mediate BMP signaling, whereas Smad2 and Smad3 respond to TGF-β (9–12). Upon phosphorylation by their type I receptors, the receptor-regulated Smads interact with a common partner, Smad4, and translocate to the nucleus where the complex recruits DNA binding protein(s) to activate specific gene transcription (1,2,13–15).

Smad6 and Smad7 are struturally divergent Smads and antagonists of TGF-β family signaling (1). Smad6 and Smad7 are characterized by the stable interactions formed with both activated TGF-β and BMP type I receptors, thereby preventing phosphorylation of ligand-induced Smads (4,5). In addition, Smad6 has also been demonstrated to interact with phosphorylated Smad1 to prevent the formation of an active signaling complex of Smad1 and Smad4, preferentially inhibiting the signaling pathways activated by bone morphogenetic proteins (7,16). Furthermore, it was previously demonstrated that Smad1 interacts with Hoxc-8 in response to BMP stimulation (13). Hoxc-8 functions as a transcriptional repressor. The interaction of Smad1 with Hoxc-8 dislodges Hoxc-8 binding from its element, thereby resulting in initiation of gene transcription (13).

In vertebrates, there are 39 Hox homeobox-containing transcription factor genes, organized into four separate chromosome clusters, which play critical roles in the process and patterning of vertebrate embryonic development (28,29). These 39 genes are subdivided into 13 paralogous groups on the basis of duplication of an ancestral homeobox cluster during evolution, sequence similarity and position within the cluster (30). Each paralog group has been demonstrated to be responsible for morphogenesis of a particular embryonic domain or structure (29). There are three members in Hox paralog group VIII, Hoxb-8, Hoxc-8 and Hoxd-8 (30). Hox genes are required during vertebrate limb bud development, and particularly, Hoxb-8 was suggested to be a transcription factor involved in activating the Sonic hedgehog gene, which is the key mediator in limb development (31,32). Furthermore, Northern blot analysis shows that Hoxc-8 is expressed during human embryo development at high levels in spinal cord, backbone and limbs and at a lower level in heart (33). BMP-2/4 activates expression of Hox genes, induces osteoblast differentiation and controls patterning across the anteroposterior (a-p) axis of developing limb (34).

The prior art is deficient in recognizing the role of Smad6 in conjunction with transcriptional regulation by Hox genes. The present invention fulfills this long-standing need and desire in the art and further provides methods of gene regulation and screening for drugs using the teachings of the present invention.

SUMMARY OF THE INVENTION

Smads are mediators of the superfamily of transforming growth factor-β (TGF-β) signaling pathways (1,2). Smad6 and Smad7, antagonize the TGF-β signals (3,4). Smad6 and Smad7, induced by TGF-β or bone morphogenetic protein (BMP), form stable associations with activated type I receptors, which, in turn, block phosphorylation of ligand-induced Smads (5,6). Smad6 also interacts with phosphorylated Smad1 to prevent the formation of an active signaling complex of Smad1 and Smad4 in the cytoplasm (7,8). Herein, it is shown that Smad6 interacts with Hoxc-8 as a transcriptional corepressor, inhibiting bone morphogenetic protein signaling in the nucleus. The present invention describes that Smad6 functions as a transcriptional corepressor in the nucleus of BMP signaling.

One object of the present invention is to describe a role for Smad6 in Hox protein transcriptional regulation, and additionally to provide methods of using the Smad6/Hox interaction in gene regulation and methods of screening for drugs that effect the Smad6/Hox interaction.

In an embodiment of the present invention, there is provided a method of regulating bone formation in an individual, comprising the step of: (a) administering a composition to the individual, wherein the composition alters the activity of Smad6 protein. An increase in the Smad6 protein results in an increase in Smad6/Hoxc-8 complexes; an increase in Smad6/Hoxc-8 complexes maintains transcriptional repression of genes involved in bone formation. A decrease in the Smad6 protein activity results in a decrease in Smad6/Hoxc-8 complexes wherein a decrease in Smad6/Hoxc-8 complexes relieves transcriptional repression of genes involved in bone formation, thereby regulating bone formation in the individual.

In another embodiment of the present invention, there is provided a method of regulating nuclear bone morphogenetic protein signaling, comprising the step of: (a) administering a composition to a cell that alters the activity of Smad6 protein. An increase in the available Smad6 protein results in an increase in Smad6/Hoxc-8 complexes; an increase in Smad6/Hoxc-8 complexes maintains transcriptional repression of genes involved in bone formation. A decrease in the Smad6 protein binding activity results in a decrease in Smad6/Hoxc-8 complexes, wherein a decrease in Smad6/Hoxc-8 complexes relieves transcriptional repression of genes involved in bone formation, thereby regulating nuclear BMP signaling.

In yet another embodiment of the present invention, there is provided a method of screening for a compound that disrupts transcriptional repression of a gene. This method comprises the steps of: (a) combining Smad6 proteins and Hoxc-8 proteins in the presence and absence of a compound; and (b) detecting complex formation between the Smad6 proteins and the Hoxc-8 proteins. A lack of complex formation between the Smad6 proteins and the Hoxc-8 proteins in the presence of the compound is indicative of a compound that disrupts transcriptional repression of a gene.

In still yet another embodiment of the present invention, there is provided a method of screening for a compound that disrupts transcriptional repression of a gene, comprising the steps of: (a) combining a Smad6/Hoxc-8 complex and a DNA molecule in the presence and absence of a compound, wherein the DNA molecule comprises a Hox DNA binding element; and (b) determining the amount of binding by the Smad6/Hoxc-8 protein complex to the DNA molecule, wherein less binding in the presence of the compound than in the absence of the compound is indicative of a compound that disrupts transcriptional repression of the gene.

In still yet another embodiment of the present invention, there is provided a method of screening for a compound that disrupts transcriptional repression of a gene, comprising the steps of: (a) combining a Smad6/Hoxc-8 protein complex with a gene in the presence and absence of a compound, wherein the gene comprises a Hox DNA binding element; and (b) assaying for transcription of the gene. An increase in the level of transcription in the presence of the compound relative to the level of transcription in the absence of the compound is indicative of a compound that disrupts transcriptional repression of the gene.

In still yet another embodiment of the present invention, there is provided a method of regulating expression of gene that binds Hoxc-8, wherein binding by Hoxc-8 results in transcriptional repression of the gene, comprising the step of: altering the binding activity of Smad6 protein. An increase in the Smad6 protein results in an increase in Smad6/Hoxc-8 protein complexes; an increase in the Smad6/Hoxc-8 protein complexes maintains the transcriptional repression of the gene. A decrease in the Smad6 protein binding activity results in a decrease in Smad6/Hoxc-8 protein complexes, wherein a decrease in Smad6/Hoxc-8 protein complexes relieves the transcriptional repression of the gene, thereby regulating expression of the gene. This method may further comprise the step of: increasing the amount of Smad1 protein, wherein the Smad1 protein binds the Hoxc-8, thereby relieving the transcriptional repression of the gene.

In still yet another embodiment of the present invention, there is provided a method of inducing transcription of a gene encoding osteopontin, comprising the steps of: inhibiting Smad6, wherein in the presence of Smad1, the inhibition of Smad6 removes transcriptional repression of a gene encoding osteopontin, thereby inducing transcription of the gene encoding osteopontin.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 3A: the complex of Smad6 and Hoxc-8 blocks the interaction of Smad1 with Hoxc-8. Gel-shift assays were performed using osteopontin Hox DNA binding element (OPN-5) as the probe (13), with 1.5 mg GST (lane 2), 1.5 mg GST-Smad1 (lanes 3, 6, 8, 10), 0.2 mg GST-Hoxc-8 protein (lanes 5–10), 1.5 mg GST-Smad6 (lanes 4, 7–10) and 0.1 mg Smad6 polyclonal antibody (Smad6AB, lanes 9 and 10).

FIG. 3B: the complex of Smad6 and Hoxc-8 moderately blocks the interaction of Smad4 with Hoxc-8. OPN-5 was used as probe, with 1.5 mg GST (lane 2), 1.5 mg GST-Smad4 (lanes 3, 5, 7 and 9), 0.2 mg GST-Hoxc-8 protein (lanes 4–9), 1.5 mg GST-Smad 6 (lanes 6–9) and 1.5 mg GST-Smad1 (lanes 9 and 10).

FIG. 4A: Smad1/Hoxc-8 interaction domain (Smad1B) induces transcription in a concentration dependent manner. Hox-pGL3 construct (500 ng), containing osteopontin Hox binding site linked to SV40 promoter, was co-transfected in Mv1Lu cells with different amounts of Smad1B expression plasmid.

FIG. 4B: The Smad6 inhibits Smad1B-induced transcription in presence of Hoxc-8. Hox-pGL3 construct was co-transfected with Smad1B (300 ng), Hoxc-8 (25 ng) or Smad6 (100 ng) expression plasmids. FIG. 4C: Mutation of Hox binding site abolishes Smad1B stimulation. mHox-pGL3 (500 ng), contains mutated osteopontin Hox binding site in Hox-pGL3 construct, was co-transfected with Smad1B (300 ng), Hoxc-8 (25 ng) or Smad6 (100 ng) plasmids. Cell lysates in A, B and C were assayed for luciferase activity normalized to Renilla luciferase levels 48 h after transfection. Experiments were repeated 3 times in triplicate.

DETAILED DESCRIPTION OF THE INVENTION

Figure 1:
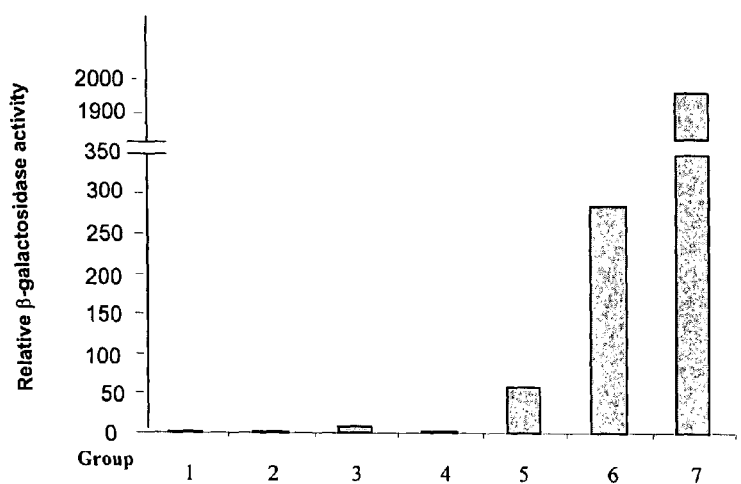
FIG. 1 shows the specific interaction of Smad6 with Hoxc-8 in a yeast two-hybrid system. The interaction was assayed in a liquid culture of yeast strain Y190, a strain which requires His, Leu and Trp to grow. pGBT9-Hoxc-8 and pACT2-Smad6 plasmids carry Trp and Leu as their selective markers, respectively. The interaction between Smad6 and Hoxc-8 enables the yeast to synthesize His and induces β-gal expression. The arbitrary units of β-gal activities for yeast bearing different plasmids were plotted as shown in the Table.

Smads are the mediators of the superfamily of transforming growth factor-β (TGF-β) signaling pathways (1, 2). Smad6 and Smad7, a subgroup of Smad proteins, antagonize the TGF-β signals (3,4). These two Smads, induced by TGF-β or bone morphogenetic protein (BMP), form stable association with activated type I receptors, which, in turn, block phosphorylation of ligand-induced Smads (5,6). Smad6 also interacts with phosphorylated Smad1 to prevent the formation of an active signaling complex of Smad1 and Smad4 in the cytoplasm (7,8).

Herein, it is shown that Smad6 interacts with Hoxc-8 as a transcriptional corepressor, inhibiting BMP signaling in the nucleus. The interaction between Smad6 and Hoxc-8 was identified in a yeast two-hybrid approach, and further demonstrated by co-immunoprecipitation assays in cells. Gel shift assays show that Hoxc-8 interacts with Smad6 as a heterodimer when binding to DNA. More importantly, the Smad6/Hoxc-8 complex inhibited both Smad1 interaction with Hoxc-8 in gel shift assays and transcription activity mediated by Smad1. The data presented herein indicate that Smad6 functions as a transcriptional corepressor in BMP signaling in the nucleus.

The present invention is directed towards methods of using the heretofore unknown interaction between Smad6 and the Hox proteins in transcriptional gene regulation, thereby producing a desired effect (i.e., regulating bone formation, controlling osteoporosis, etc.). A method of screening for compounds that disrupt the Smad6/Hox protein complex is further provided.

The present invention is directed towards a method of regulating bone formation in an individual, comprising the step of:

(a) administering a composition to the individual, wherein the composition alters the binding activity of Smad6 protein, wherein an increase in the Smad6 protein results in an increase in Smad6/Hoxc-8 complexes, wherein an increase in Smad6/Hoxc-8 complexes maintains transcriptional repression of genes involved in bone formation, wherein a decrease in the Smad6 protein binding activity results in a decrease in Smad6/Hoxc-8 complexes, wherein a decrease in Smad6/Hoxc-8 complexes relieves transcriptional repression of genes involved in bone formation, thereby regulating bone formation in the individual.

The present invention is directed towards a method of regulating nuclear BMP signaling, comprising the step of: (a) administering a composition to a cell, wherein the composition alters the binding activity of available Smad6 protein, wherein an increase in the available Smad6 protein results in an increase in Smad6/Hoxc-8 complexes, wherein an increase in Smad6/Hoxc-8 complexes maintains transcriptional repression of genes involved in bone formation, wherein a decrease in the Smad6 protein binding activity results in a decrease in Smad6/Hoxc-8 complexes, wherein a decrease in Smad6/Hoxc-8 complexes relieves transcriptional repression of genes involved in bone formation, thereby regulating nuclear BMP signaling. Representative compositions are selected from the group consisting of a gene encoding Smad6, an antisense molecule directed towards Smad6, an antibody directed towards Smad6. Generally, the genes involved in bone formation are selected from the group consisting of osteopontin, osteoprotegrin, RANK and OPGL.

The present invention is directed towards a method of screening for a compound that disrupts transcriptional repression of a gene, comprising the steps of: (a) combining Smad6 proteins and Hoxc-8 proteins in the presence and absence of a compound; and (b) detecting complex formation between the Smad6 proteins and the Hoxc-8 proteins, wherein a lack of complex formation between the Smad6 proteins and the Hoxc-8 proteins in the presence of the compound is indicative of a compound that disrupts transcriptional repression of a gene. Representative means of detection are a gel shift assay and a Western blot.

The present invention is directed towards a method of screening for a compound that disrupts transcriptional repression of a gene, comprising the steps of: (a) combining a Smad6/Hoxc-8 complex and a DNA molecule in the presence and absence of a compound, wherein the DNA molecule comprises a Hox DNA binding element; and (b) determining the amount of binding by the Smad6/Hoxc-8 protein complex to the DNA molecule, wherein less binding in the presence of the compound than in the absence of the compound is indicative of a compound that disrupts transcriptional repression of the gene. Typically, DNA binding by the Smad6/Hoxc-8 protein complex is determined by means selected from the group consisting of a gel-shift assay, a competitive binding assay, immunoprecipitation and Yeast two-hybrid assay.

The present invention is directed towards a method of screening for a compound that disrupts transcriptional repression of a gene, comprising the steps of: (a) combining a Smad6/Hoxc-8 protein complex with a gene in the presence and absence of a compound, wherein the gene comprises a Hox DNA binding element; and (b) assaying for transcription of the gene, wherein an increase in the level of transcription in the presence of the compound relative to the level of transcription in the absence of the compound is indicative of a compound that disrupts transcriptional repression of the gene. Generally, transcription is assayed by means selected from the group consisting of a Northern blot, a Western blot, an enzymatic assay and a chemiluminescent assay. Preferably, the gene is a reporter gene, and more preferably, the reporter gene is selected from the group consisting of β-galactosidase, luciferase, secreted alkaline phosphotase and CAT assay.

The present invention is directed towards a method of regulating expression of gene that binds Hoxc-8, wherein binding by Hoxc-8 results in transcriptional repression of the gene, comprising the step of: altering the amount of Smad6 protein, wherein an increase in the Smad6 protein results in an increase in Smad6/Hoxc-8 protein complexes, wherein an increase in the Smad6/Hoxc-8 protein complexes maintains the transcriptional repression of the gene, wherein a decrease in the Smad6 protein results in a decrease in Smad6/Hoxc-8 protein complexes, wherein a decrease in Smad6/Hoxc-8 protein complexes relieves the transcriptional repression of the gene, thereby regulating expression of the gene. Representative genes are osteopontin, osteoprotegrin, OPGL and RANK. Typically, the Smad6 protein is increased by means selected from the group consisting of overexpression of a Smad6 gene and upregulation of a Smad6 gene, or alternatively, the Smad6 protein is decreased by means selected from the group consisting of antisense hybridization to Smad6 RNA, antibody binding to a Smad6 protein and mutagenesis of a gene encoding Smad6. This method may further comprise the step of: increasing the amount of Smad 1 protein, wherein the Smad1 protein binds the Hoxc-8, thereby relieving the transcriptional repression of the gene.

The present invention is directed towards a method of inducing transcription of a gene encoding osteopontin, comprising the steps of: inhibiting Smad6, wherein in the presence of Smad 1, the inhibition of Smad6 removes transcriptional repression of a gene encoding osteopontin, thereby inducing transcription of the gene encoding osteopontin.

As used herein, the term "transcriptional repression by a hox protein" or "transcriptional repression by a homeodomain-containing protein" shall refer to any gene whose transcription activities are repressed in the presence of the hox protein or the homeodomain-containing protein.

The following examples are given for the purpose of illustrating various embodiments of the invention and are not meant to limit the present invention in any fashion:

EXAMPLE 1

Two-hybrid Library Screening

A full-length Hoxc-8 coding sequence was cloned into pGBT9 (CLONTECH) to generate the pGBT9/Hoxc-8 bait plasmid. The human U2 OS osteoblast-like pACT2 cDNA library was screened with the pGBT9/Hoxc-8 bait plasmid according to the manufacturer's instruction (CLONTECH).

EXAMPLE 2

Immunoprecipitation and Western Blot

Figure 2:
FIG. 2 shows the interaction of Smad1 with Hoxc-8 in vivo. Flag-tagged Smad6, Flag-tagged Smad6 carboxy domain (Smad6C), Flag-tagged Smad6 amino domain with linker region (Smad6 N+L) and HA-tagged Hoxc-8 were co-transfected in COS-1 cells with or without ALK3 (Q233D). Cell lysates were immunoprecipitated by anti-Flag antibody and the resulted complexes were analyzed by Western blotting with anti-HA antibody. The expression levels of Smad6 were shown by Western blot with anti-Flag antibody (middle panel), and Hoxc-8 with anti-HA antibody (bottom panel).
Figure 2:
Figure 2:

Expression vectors for Flag-tagged full length Smad6, amino-domain with linker region (Smad6NL) and carboxy-domain (Smad6C) were subcloned into a mammalian expression vector pcDNA3 (Invitrogen). HA-tagged Hoxc-8 expression vector was constructed (13). Constitutively active BMP type IA (ALK3) expression plasmid was provided by Dr. Jeffrey L. Wrana (The Hospital for Sick Children, Canada). COS-1 cells were transfected with expression constructs as indicated in FIG. 2 using Tfx-50 according to manufacturer's description (Promega). Cells were lysed 48 h post-transfection and lysates were immunoprecipitated with anti-Flag M2 antibody (Eastman Kodak) and immuno-blotted with anti-HA antiserum (Babco).

EXAMPLE 3

Gel Shift Assay

Gel-shift assays were performed (26). Smad 1 and 4 cDNAs were obtained from Dr. R. Derynck. GST-fusion constructs of Smad1 and 4 and Hoxc-8 were generated (13). Smad6 cDNA, obtained from Dr. Ali Hemmati-Brivanlou, was cloned into pGEX-KG vector. The GST-constructs described above were transformed into BL21. The expression and purification of the fusion proteins were performed (27). OPN5 DNA fragments were used for the gel shift assays (13).

EXAMPLE 4

Transfection

Hox-pGL3 reporter bearing Hoxc-8 binding site (−290 to −166) was constructed into pGL3-control vector (Promega). The Hox recognition core TAAT was replaced with GCCG in Hox-pGL3 by PCR to create mutant Hox-pGL3 (mHox-pGL3). Mv1Lu cells (5×$10^4$ cells/22.6 mm dish) were transfected using Tfx-50 with 0.5 mg of luciferase reporter plasmid (Hox-pGL3 or mHox-pGL3) and different expression plasmids as indicated. Total DNA was kept constant by addition of pcDNA3 plasmid. Luciferase activities were assayed 48 h post-transfection using the Dual Luciferase Assay Kit (Promega) according to manufacturer's direction. Luciferase values shown in the figures are representative of transfection experiments performed in triplicate in at least three independent experiments.

EXAMPLE 5

Identification of Transcription Factors that Interact with Hoxc-8

To characterize the Hoxc-8-mediated transcription mechanism in bone morphogenetic protein-induced gene activation, a yeast two-hybrid system was used to identify transcription factors that interact with Hoxc-8. An intact Hoxc-8 cDNA fused with the Gal4 DNA binding domain was used as a bait plasmid to screen a human U-2 OS osteoblast-like cell cDNA library constructed in pACT2 plasmid. After two rounds of screening, 26 positive clones were obtained. DNA sequence analysis identified one clone as Smad6 (FIG. 1). Smad6 and Smad7 are immunolocalized in the nucleus of rat epiphyseal plate (17), Xenopus embryo (18) and Mink lung epithelial (Mv1Lu) cells (19). The interaction of Smad6 with Hoxc-8, a transcription repressor in bone morphogenetic protein signaling pathway, suggests that Smad6 may have a novel antagonistic function in the nucleus.

The initial Smad6 cDNA clone (Smad6C in FIG. 1) encodes amino acids 281 to 496 out of a 496 amino acid protein. The interaction between Hoxc-8 and Smad6 was further confirmed with a β-gal filter lift assay and quantified by a liquid β-gal assay (FIG. 1). When the full length Smad6 fused with the Gal4 transcriptional activation domain was tested in the two-hybrid system, it showed a weaker interaction compared with the carboxy-terminal domain (Smad6C). Deletion of Smad6 amino-terminal domain may change the protein conformation such that the carboxy-terminal region becomes available to interact with Hoxc-8. The assays of both empty bait vector (pGBT9) with either Smad6C or Smad6 full length cDNAs in prey plasmids as well as empty prey vector (pACT9) with full length Hoxc-8 in bait vector showed very little activity. Compared with the interaction between Smad1 and Hoxc-8, the interaction of Smad6 with Hoxc-8 is about 5-fold stronger (FIG. 1).

EXAMPLE 6

The Interaction of Smad6 with Hoxc-8 in Mammalian Cells

To investigate the interaction of Smad6 with Hoxc-8 in mammalian cells and the effect of bone morphogenetic protein stimulation on this interaction, COS-1 cells were transiently co-transfected with expression plasmids for Flag-Smad6, HA-Hoxc-8, and/or constitutively active bone morphogenetic protein type IA receptor ALK3 (Q233D). The cell lysates were immunoprecipitated with anti-Flag antibody and immuno-blotted with anti-HA antibody. The results in FIG. 2 demonstrate that Smad6 (lanes 7 and 8) was co-immunoprecipitated with HA-Hoxc-8.

Overexpression of ALK3 (Q233D) did not change the interaction of Smad6 with Hoxc-8 (lane 8), indicating that bone morphogenetic protein stimulation is not required for the interaction between Smad6 and Hoxc-8. Since bone morphogenetic protein induces Smad6 mRNA expression (20–22), these data suggest that bone morphogenetic protein regulates the interaction between Smad6 and Hoxc-8 at the level of Smad6 transcription. The initial Smad6 clone only encodes the carboxy-terminal domain, indicating that this region of the protein may be involved in the interaction with Hoxc-8.

To further investigate this observation, two Flag-tagged Smad6 truncated expression plasmids were constructed. As shown in FIG. 2, Smad6C exhibits a strong interaction with Hoxc-8 (lanes 4 and 5). In contrast, the Smad6 amino-terminal with linker region (Smad6NL) failed to bind to Hoxc-8 in immuno-precipitation assay (FIG. 2, lane 6). Smad proteins contain highly conserved carboxy- and amino-terminal domains (referred to as MH1 and MH2 domains, respectively). The MH1 domain inhibits biological activities of the MH2 domain due to interactions between these two distal sites (23). Like other regulatory Smads, Smad6 also contains a conserved MH2 domain and short segments of MH1 domain homology (24). Therefore, results herein suggest that the carboxy-terminal domain of Smad6 interacts with Hoxc-8, and that the amino-terminus negatively regulates interaction between the two proteins.

EXAMPLE 7

The Effect of Hoxc-8/Smad6 on Hoxc-8 DNA Binding Activity

Next, the effect of the interaction between Hoxc-8 and Smad6 on Hoxc-8 DNA binding activity was examined. Gel shift assays were performed with purified GST-Smad6 and GST-Hoxc-8 fusion proteins and using osteopontin Hoxc-8 DNA binding element as a probe.

Figure 3:
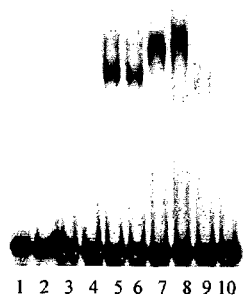
FIGS. 3a–3b that the Smad6 and Hoxc-8 form a complex on Hox DNA binding site from osteopontin promoter.
Figure 3:
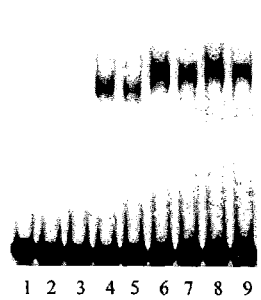

As expected, Hoxc-8 protein binds to the DNA probe, which is inhibited by Smad1 (FIG. 3A, lanes 5 and 6). Smad6 alone did not bind to the DNA element (lane 4). Interestingly, incubation of both Hoxc-8 and Smad6 proteins yields a distinct shifted band with a molecular weight higher than Hoxc-8 binding alone, indicating that Hoxc-8 and Smad6 bind to the DNA element cooperatively (lane 7). More importantly, the formation of the Smad6 and Hoxc-8 complex blocked the interaction of Hoxc-8 with Smad1 (lane 8). Yeast two-hybrid assays already demonstrated that the interaction between Hoxc-8 and Smad6 is much stronger than that between Hoxc-8 and Smad1 (FIG. 1).

The formation of the complex between Hoxc-8 and Smad6 on the DNA element was confirmed by the fact that an anti-Smad 6 polyclonal antibody inhibited the development of the retarded band (lanes 9 and 10). Smad4, also interacting with Hoxc-8, was examined for the same purpose in gel shift assays (FIG. 3B). The complex of Smad6 and Hoxc-8, however, did not block the interaction of Smad4 with Hoxc-8 completely (FIG. 3B, lanes 7 and 9). In fact, it has been shown that Smad6 inhibits Smad1 phosphorylation and prevents its translocation into nucleus (5,7), whereas Smad4, a common partner for all regulatory Smads, can only be passively translocated into nucleus by forming hetero-oligomers with regulatory Smads (25). Therefore, the preference of Smad6 inhibition for Smad1-mediated gene transactivation suggests the importance of Smad6 antagonistic function for BMP signaling pathway.

EXAMPLE 8

Figure 4:
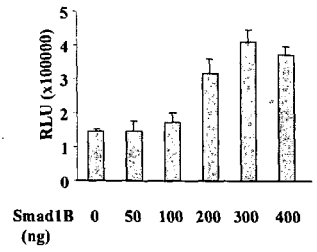
FIGS. 4a–4c that BMP-induced osteopontin gene transcription is mediated by Hoxc-8 binding site.
Figure 4:
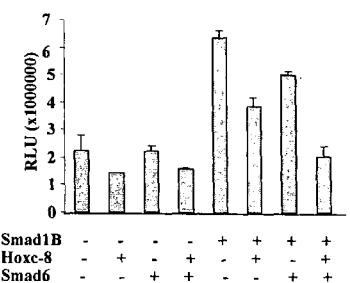
Figure 4:
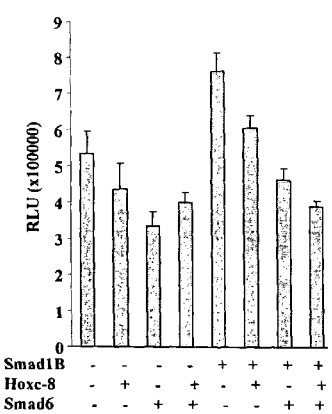

Inhibition of Smad1/Hoxc-8-activated Gene Transcription by the Smad6/Hoxc-8 Complex To investigate whether the Smad6/Hoxc-8 complex inhibits the interaction of Smad1 with Hoxc-8 in activating gene transcription, a model was used (13). The interaction domains within the amino-terminal 87 amino acid residues of Smad1 were mapped to interact with Hoxc-8. Overexpression of cDNAs encoding the Hoxc-8 interaction domains of Smad1 linked to a nuclear localization signal (Smad1B) effectively activated osteopontin gene transcription. Stable expression of these Smad1 fragments in 2T3 osteoblast precursor cells stimulated endogenous osteoblast differentiation-related gene expression and mineralized bone matrix formation. When the BMP-inducible construct (Hox-pGL3) was co-transfected into Mv1Lu cells with the Smad1B expression plasmid, luciferase activity was stimulated in a dose-dependent manner (FIG. 4A). This model provides an ideal assay to examine the Smad6 antagonistic function in the nucleus directly. Because Smad1B mimics BMP-induced gene transcription without involving BMP receptor phosphorylation and interaction with Smad (67), this assay avoids Smad6 inhibitory function in the cytoplasm.

Hox-pGL3 construct was co-transfected in Mv1Lu cells with Hoxc-8 or Smad6 expression plasmid, or both. As shown in FIG. 4B, overexpression of Hoxc-8 or Smad6 alone inhibited Smad1B-induced transcription activity. In addition to the interaction between Smad6 and Hoxc-8 in the nucleus, Smad6 binds to BMP type I receptor to block phosphorylation of other regulatory Smads. Smad6 has also been shown to interacted with phosphorylated Smad1, inhibiting Smad1 translocated into nucleus. Most importantly, co-transfection of both Hoxc-8 and Smad6 plasmids completely abolished the Smad1B-induced luciferase activity. To validate this observation, Mv1Lu cells were transfected with a mutated construct (mHox-pGL3) in which the core nucleotides of the Hoxc-8 binding site were mutated from TAAT to GCCG. As expected, transfection of the mutant construct completely abolished Smad1B-induced reporter activity and eliminated Smad6/Hoxc-8 complex-mediated inhibition (FIG. 4C). These results demonstrate for the first time that Smad6 has an antagonistic function towards BMP signaling in the nucleus in addition to its interaction with BMP type I receptor and Smad1 in the cytoplasm.

The following references were cited herein:
1. Massague, J. Annu. Rev. Biochem. 67, 753–791(1998).
2. Heldin, C-H., et al. Nature 390, 465 (1997).
3. Hayashi, H., et al. Cell 89, 1165–1173 (1997).
4. Nakao, A., et al. Nature 389, 631–635 (1997).
5. Imamura, T., et al. Nature 389, 622–626 (1997).
6. Kawabata, M., et al. Cytokine & Growth Factor Reviews 9, 49–61 (1998).
7. Hata, A., et al. Genes Dev. 12, 186–197 (1998).
8. Dennler, S., et al. EMBO J. 17, 3091–3100 (1998).
9. Hoodless, P. A., et al. Cell 85, 489–500 (1996).
10. Nishimura, R., et al. J. Biol. Chem. 273, 1872–1879 (1998).
11. Nakayama, T., et al. Development. 125, 857–867 (1998).
12. Nakao, A., et al. EMBO J. 16(17), 5353–5362 (1997).
13. Shi, X. M., et al. J. Biol. Chem. 274, 13711–13717 (1999).
14. Chen, X., et al. Nature 389, 85–89 (1997).
15. Hua, X., et al. Genes Dev. 12, 3084–3095 (1998).
16. Ishisaki, A., et al. J. Biol. Chem. 274, 13637–13642 (1999).
17. Sakou, T., et al. J Bone Miner Res. 14, 1145–1152 (1999).
18. Nakayama, T., et al. Genes to Cells 3, 387–394 (1998).
19. Itoh, S., et al. J. Biol. Chem. 273, 29195–29201 (1998).
20. Afrakhte, M., et al. Biochem Biophys Res Commun. 249, 505–511 (1998).
21. Takase, M., et al. Biochem Biophys Res Commun. 244, 26–9 (1998).
22. Ishisaki, A., et al. Biol. Chem. 274, 13637–13642 (1999).
23. Shi, Y., et al. Cell 94, 585–594 (1998).
24. Newfeld, S. J., et al. Genetics 152, 783–795 (1999).
25. Liu, F., et al. Genes Dev 11, 3157–3167 (1997).
26. Cao, X., et al. J. Biol. Chem. 271, 20650–20654 (1996).
27. Sterner, J. M., et al. J. Biol. Chem. 270, 9281–9288 (1995).
28. Hunt, P. & Krumlauf, R. Annu. Rev. Cell Biol. 8, 227–256 (1992).
29. Sharkey, M., et al. TIG 13, 145–151 (1997).
30. Maconochie, M., et al. Annu. Rev. Genet. 30, 529–556 (1996).
31. Charite, J., et al. Cell 78, 589–601 (1994).
32. Lu, H. C., et al., Development 124, 1643–1651 (1997).
33. Simeone, A., et al. Proc. Natl. Acad. Sci. USA 84, 4914–4918 (1987).
34. Hardy, A., et al. Development 121, 4329–4337 (1995).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening for a compound that disrupts transcriptional repression of a gene, comprising the steps of:
    (a) combining a Smad6/Hoxc-8 protein complex with a gene in the presence and absence of a compound, wherein said gene comprises a Hox DNA binding element; and
    (b) assaying for transcription of said gene, wherein an increase in the level of transcription in the presence of said compound relative to the level of transcription in the absence of said compound is indicative of a compound that disrupts transcriptional repression of said gene.

2. The method of claim 1, wherein said transcription is assayed by means selected from the group consisting of a Northern blot, a Western blot, an enzymatic assay and a chemiluminescent assay.

3. The method of claim 1, wherein said gene is a reporter gene.

4. The method of claim 3, wherein said reporter gene is selected from the group consisting of β-galactosidase, luciferase, secreted alkaline phosphotase and CAT assay.

* * * * *